United States Patent
Cao et al.

(10) Patent No.: US 11,969,199 B2
(45) Date of Patent: Apr. 30, 2024

(54) BIPOLAR IRRIGATED RADIOFREQUENCY ABLATION TINED PROBE

(71) Applicant: Boston Scientific Scimed, Inc., Maple Grove, MN (US)

(72) Inventors: Hong Cao, Maple Grove, MN (US); Timothy A. Ostroot, Cokato, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 834 days.

(21) Appl. No.: 16/526,738

(22) Filed: Jul. 30, 2019

(65) Prior Publication Data
US 2020/0038091 A1    Feb. 6, 2020

Related U.S. Application Data

(60) Provisional application No. 62/713,257, filed on Aug. 1, 2018.

(51) Int. Cl.
*A61B 18/14* (2006.01)
*A61B 18/00* (2006.01)
(Continued)

(52) U.S. Cl.
CPC ........ *A61B 18/082* (2013.01); *A61B 18/1206* (2013.01); *A61B 18/14* (2013.01); *A61B 2018/00029* (2013.01); *A61B 2018/00577* (2013.01); *A61B 2018/00642* (2013.01); *A61B 2018/00875* (2013.01); *A61B 2018/126* (2013.01); *A61B 2018/143* (2013.01); *A61B 2018/1467* (2013.01);
(Continued)

(58) Field of Classification Search
CPC ................ A61B 18/14; A61B 18/1477; A61B 2018/00029; A61B 2018/126; A61B 2018/1467; A61B 2018/1475
See application file for complete search history.

(56) References Cited

U.S. PATENT DOCUMENTS 5,348,554 A    9/1994  Imran et al.
5,807,395 A    9/1998  Mulier et al.
(Continued)

FOREIGN PATENT DOCUMENTS

JP    2016185295    10/2016
JP    7179957    11/2022
(Continued)

OTHER PUBLICATIONS

"Advancing Ablation Boundaries," RFA Medical Technology and Product Information accessed from website URL <www.rfamedical.com> on Sep. 10, 2019 (2018) 4 pages.

Bruners, Philipp et al., "A Newly Developed Perfused Unbrella Eletrode for Radiofrequency Ablation: An Ex Vivo Evaluation Study in Bovine Liver," Cardiovasc Intervent Radiol (2007) 30:992-998 (7 pages).

(Continued)

*Primary Examiner* — Joseph A Stoklosa
*Assistant Examiner* — Annie L Shoulders
(74) *Attorney, Agent, or Firm* — Pauly, DeVries Smith & Deffner LLC

(57) ABSTRACT

The disclosure relates to systems and methods for irrigated bipolar radiofrequency ablation. Some examples of the system include an elongate inner electrode assembly and an elongate outer electrode assembly. An irrigation path for irrigation fluid flow is defined between the outer surface of the inner electrode assembly and the outer surface of the outer electrode assembly.

19 Claims, 9 Drawing Sheets

(51) Int. Cl.
  *A61B 18/08* (2006.01)
  *A61B 18/12* (2006.01)
(52) U.S. Cl.
  CPC ... *A61B 2018/1475* (2013.01); *A61B 18/1477* (2013.01); *A61B 2218/002* (2013.01)

(56) References Cited

U.S. PATENT DOCUMENTS

| | | | |
|---|---|---|---|
| 5,855,576 | A | 1/1999 | Leveen et al. |
| 5,868,740 | A | 2/1999 | Leveen et al. |
| 6,905,489 | B2 * | 6/2005 | Mantell ............ A61B 17/3496 600/3 |
| 7,942,873 | B2 | 5/2011 | Kwan et al. |
| 8,414,580 | B2 | 4/2013 | Rioux et al. |
| 9,770,290 | B2 | 9/2017 | Young et al. |
| 9,956,032 | B1 * | 5/2018 | Cosman ............ A61B 18/1477 |
| 2005/0137659 | A1 | 6/2005 | Garabedian et al. |
| 2005/0234443 | A1 * | 10/2005 | Rioux ................ A61B 18/00 606/41 |
| 2009/0131855 | A1 | 5/2009 | Young et al. |
| 2010/0198210 | A1 * | 8/2010 | Lanphere ........... B01J 13/0056 514/779 |
| 2011/0077644 | A1 * | 3/2011 | Pham ................. A61B 18/1477 606/41 |
| 2011/0288541 | A1 | 11/2011 | Faure |
| 2018/0132922 | A1 * | 5/2018 | Neal, II ............. A61N 1/0412 |
| 2019/0374277 | A1 * | 12/2019 | Bagwell ............. A61B 18/14 |

FOREIGN PATENT DOCUMENTS

| | | |
|---|---|---|
| WO | 2005104973 | 11/2005 |
| WO | 2020028543 | 2/2020 |

OTHER PUBLICATIONS

"Delivering Energy Innovation: The New Cool-tip RF Ablation System E Series," Coviden Cool-tip Product Brochure Feb. 2014 (4 pages).
Ito, Nobutake et al., "Bipolar Radiofrequency Ablation: Development of a New Expandable Device," Cardiovasc Intervent Radiol (2014) 37:770-776 (7 pages).
"Leveen Needle Electrodes," Boston Scientific Corporation product information for Leveen Needle Electrode Family, Jul. 2015 (2 pages).
Narayanan, G et al., "Radiofrequency Ablation: Current Status," Boston Scientific Corporation Technique Spotlight, Jun. 2015 (8 pages).
"OsteoCool RF Ablation System and Bone Access Kits," Medtronic Surgical Technique Guide 2019 (16 pages).
"OsteoCool RF Ablation System," Medtronic Product Brochure 2019 (6 pages).
"RF 3000 Generator," Boston Scientific Corporation Product Brochure, Jun. 2015 (6 pages).
"StarBurst XL Radiorequency Ablation Alectrodes," Angiodynamics Product Brochure, 2013 (2 pages).
"International Search Report and Written Opinion," for PCT Application No. PCT/US2019/044451 dated Nov. 13, 2019 (16 pages).
"International Preliminary Report on Patentability," for PCT Application No. PCT/US2019/044451 dated Feb. 11, 2021 (11 pages).
"Office Action," for Japanese Patent Application No. 2021-505231 dated Mar. 15, 2022 (5 pages) No English Translation.
"Response to Communication Pursuant to Rules 161(1) and 162 EPC," for European Patent Application No. 19752845.8 filed Jul. 21, 2021 (14 pages).
"First Office Action," for CN Patent Application No. 201980050801.X mailed Jan. 6, 2024 (5 pages).

* cited by examiner

BIPOLAR IRRIGATED RADIOFREQUENCY ABLATION TINED PROBE

This application claims the benefit of U.S. Provisional Application No. 62/713,257, filed Aug. 1, 2018, the content of which is herein incorporated by reference in its entirety.

BACKGROUND

Radiofrequency ablation is used in the treatment of medical conditions, including the treatment of tumors. In this context, one goal of radiofrequency ablation is to destroy the tumor, forming a lesion. Radiofrequency ablation heats and dehydrates tissue, causing necrosis and tissue charring. Charred tissue acts as an insulator and causes increased impedance in the tissue. Radiofrequency energy cannot penetrate tissue with a high impedance. The charred tissue prevents the delivery of radiofrequency energy deeper into the tissue. In some situations, this effect limits the size of the lesion created by the radiofrequency ablation treatment.

SUMMARY

One aspect of the disclosed technology provides a system for bipolar irrigated radiofrequency ablation that includes an elongate inner electrode assembly and an elongate outer electrode assembly. In some examples, the elongate inner electrode assembly includes a distal end, a proximal end, and an outer surface. In some examples, the inner electrode assembly has a sheath, a first lead within the sheath, and an electrode array comprising three or more electrode tines positioned at the distal end of the inner electrode assembly and electrically connected to the first lead. In some examples, this electrode array is moveable between a first position contained within the sheath and a second position protruding from a distal end of the sheath. In some examples, the elongate outer electrode assembly has a distal end and a proximal end, and the outer electrode assembly has a cannula with a distal end and a proximal end. In some examples, the outer electrode assembly includes an inner surface defining a lumen, a shaft electrode near the distal end of the cannula on an outer surface of the outer electrode assembly, and a conductive path from the proximal end of the outer electrode assembly to the shaft electrode. Some examples further provide an irrigation path defined between the outer surface of the inner electrode assembly and an outer surface of the outer electrode assembly, and some examples further provide that the inner electrode assembly is configured to be positioned within the lumen of the outer electrode assembly, and the system is configured for attaching to a generator to provide radiofrequency current flow between the electrode array and the shaft electrode.

Further examples of the disclosed technology can have one or more alternative or additional features. Alternatively or in addition, one or more examples of the technology further includes an insulation layer between the inner electrode assembly and the outer electrode assembly, and the insulation layer can be an insulation sheath positioned on the outer surface of the inner electrode assembly, or an insulating coating on the inner surface of the outer electrode assembly.

Alternatively or in addition, one or more examples of the technology further include an insulation layer between the inner electrode assembly and the outer electrode assembly, and the insulation layer comprises an insulation sheath positioned on the outer surface of the inner electrode assembly, and a distal segment of the insulation layer protrudes from the distal end of the outer electrode assembly.

Alternatively or in addition, in one or more examples of the technology, the irrigation path is defined between an outer surface of the inner electrode assembly and the inner surface of the outer electrode assembly, and further defined by irrigation openings defined in the shaft electrode.

Alternatively or in addition, in one or more examples of the technology, the outer electrode assembly has a proximal insulating segment adjacent to an outer surface of the cannula, and the proximal insulating segment extends from near the proximal end of the cannula to the shaft electrode. In some examples, the irrigation path is defined between the outer surface of the cannula and an inner surface of the proximal insulating segment.

Alternatively or in addition, in one or more examples of the technology, the shaft electrode is attached to the outer surface of the cannula, and the cannula defines irrigation openings near the shaft electrode. In some examples, the irrigation path is defined between the inner surface of the cannula and the outer surface of the inner electrode assembly.

Alternatively or in addition, in one or more examples of the technology, the shaft electrode is attached to the outer surface of the cannula and the cannula defines irrigation openings near the shaft electrode. In some examples, the irrigation path is defined within a wall of the cannula and through the irrigation openings.

Alternatively or in addition, in one or more examples, the irrigation path is defined through irrigation openings defined in the shaft electrode or defined near the shaft electrode.

Alternatively or in addition, in one or more examples the cannula includes a cannula body made of a conductive material, and the shaft electrode is formed by an exposed segment of the conductive material. The cannula can further include a proximal insulating segment on an outer surface of the cannula body extending from near the proximal end of the cannula body to the shaft electrode, the proximal insulating segment comprising an insulating tubing layer on an outer surface of the cannula body.

Alternatively or in addition, in one or more examples, the cannula body comprises stainless steel and wherein at least a portion of the outer surface of the cannula body is rough, textured, or threaded.

Alternatively or in addition, in one or more examples, the insulating tubing layer of the proximal insulating segment can be polyimide tubing, polyimide tubing with braided fibers within a wall of the tubing, polyethylene terephthalate (PET), polyether ether ketone (PEEK), and polytetrafluoroethylene (PTFE).

Alternatively or in addition, in one or more examples further include a distal insulating segment at the distal end of the cannula body comprising an insulating layer on an outer surface of the cannula body. Alternatively or in addition, the insulating layer of the distal insulating segment can me a heat shrink material, polyether ether ketone (PEEK), polytetrafluoroethylene (PTFE), fluoropolymers, fluorinated ethylene propylene (FEP), polyethylene terephthalate (PET), and combinations of these materials.

Alternatively or in addition, in one or more examples, the cannula has a cannula body made of an insulating material, and the shaft electrode is attached to an outer surface of the cannula body. In one or more examples, a second lead provides a conductive path from the proximal end of the cannula to the shaft electrode within a wall of the cannula body.

Alternatively or in addition, in one or more examples, the inner electrode assembly defines a central passage and an opening at the distal end of the inner electrode assembly, the system further comprising a stylet configured to be received within the central passage of the inner electrode assembly, the stylet comprising a sharp tip.

Alternatively or in addition, the irrigation path defines an exit path for open irrigation.

One aspect of the disclosed technology provides a system for bipolar irrigated radiofrequency ablation that includes an elongate inner electrode assembly and an elongate outer electrode assembly. In some examples, the elongate inner electrode assembly has a distal end, a proximal end, and an outer surface. In some examples, the inner electrode assembly includes a sheath, a first lead within the sheath, an electrode array comprising three or more electrode tines positioned at the distal end of the inner electrode assembly and electrically connected to the first lead, wherein the electrode array has a first position contained within the sheath and a second position protruding from a distal end of the sheath, and an insulation sleeve positioned on the outer surface of the sheath. In some examples, the elongate outer electrode assembly has a distal end and a proximal end, and the elongate outer electrode assembly includes a cannula having a cannula body made of an electrically conductive material, an inner surface defining a lumen, a shaft electrode formed by an exposed segment of the conductive material of the cannula on an outer surface of the outer electrode assembly, and a proximal insulating segment on the outer surface of the cannula body extending from near the proximal end of the cannula body to the shaft electrode. In some examples, an irrigation path is defined between the outer surface of the inner electrode assembly and the inner surface of the cannula, and the irrigation path is further defined through irrigation openings defined in the shaft electrode. In some examples, the inner electrode assembly is configured to be positioned within the lumen of the outer electrode assembly and the system is configured for attaching to a generator to provide radiofrequency current flow between the electrode array and the shaft electrode.

In another aspect, the disclosed technology provides a radiofrequency ablation method that includes the steps of providing an elongate inner electrode assembly having a distal end, a proximal end, and an outer surface. In some examples, the inner electrode assembly has a sheath, an electrode array comprising three or more electrode tines positioned at the distal end of the inner electrode assembly and electrically connected to a first lead, and the electrode array is moveable between a first position contained within the sheath and a second position protruding from a distal end of the sheath. In some examples, the method further includes the step of providing an elongate outer electrode assembly having a distal end and a proximal end and comprising a cannula having a distal end and a proximal end. In some examples, the cannula has an inner surface defining a lumen, a shaft electrode near the distal end of the cannula on an outer surface of the outer electrode assembly, and a conductive path from the proximal end of the cannula to the shaft electrode. In some examples, the method further includes the steps of positioning the inner electrode assembly within the cannula of the outer electrode assembly, attaching an irrigation source to an irrigation path defined between the outer surface of the inner electrode assembly and the outer surface of the outer electrode assembly, providing fluid flow through the irrigation path, and attaching the inner electrode assembly and outer electrode assembly to a generator and providing radiofrequency current flow between the electrode array and the shaft electrode.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

Figure 1A:
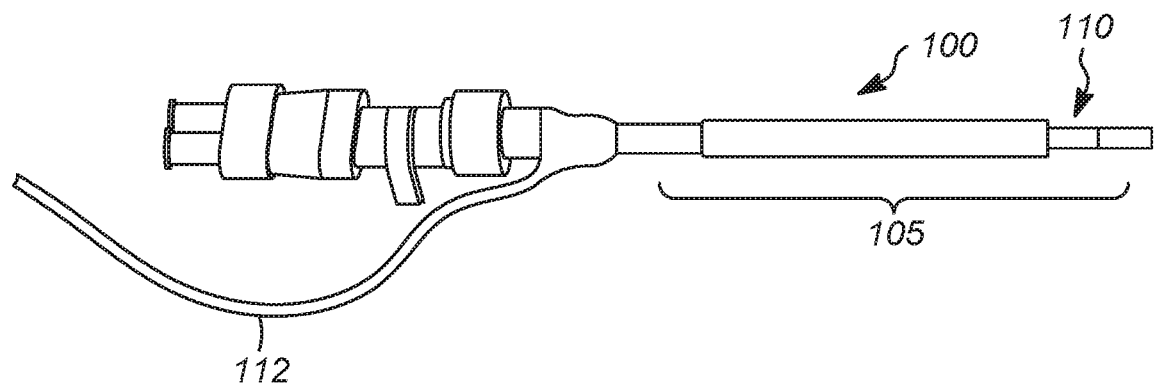
FIG. 1A is a side view of a proximal outer electrode assembly of a bipolar, open irrigated, radiofrequency ablation system according to some examples.

While embodiments herein are susceptible to various modifications and alternative forms, specifics thereof have been shown by way of example and drawings, and will be described in detail. It should be understood, however, that the scope herein is not limited to the particular examples described. On the contrary, the intention is to cover modifications, equivalents, and alternatives falling within the spirit and scope herein.

DETAILED DESCRIPTION

This disclosure describes a radiofrequency ablation system with open irrigation and bipolar electrodes to enhance lesion formation for soft tissue ablation. The system can significantly improve the ablation performance over existing radiofrequency ablation systems. The disclosed technology provides larger lesions in a shorter application time. The improved performance is competitive with other energy systems such as microwave ablation, creating a lesion similar in size in a similar amount of time as microwave ablation methods.

In various examples of the technology, open irrigation cools down the temperature of the electrode and the surrounding tissue, which allows higher power and long duration for radiofrequency energy delivery. A coolant takes heat away from the electrode and surrounding tissue to prevent or slow tissue charring during radiofrequency ablation. It also can create an area of high conductivity fluid surrounding the radiofrequency ablation probe electrodes. This results in less resistive heating near the electrodes. Another result is spreading current density over a larger portion of the tissue. The open irrigation system rehydrates tissue for better thermal and electrical conductivity during radiofrequency ablation. Higher power application creates a deeper energy penetration into tissue. This allows for a longer duration for heat to conduct further to form the lesion before charring occurs.

This disclosure describes a bipolar radiofrequency ablation system where the majority of the energy is delivered locally, bounded by two electrodes. The more local delivery of energy compared to monopolar radiofrequency ablation, which uses ground pads on the patient's skin, has the advantages of more efficient energy delivery and faster lesion formation. Also, lesion formation is more consistent because energy delivery does not involve the rest of the patient body. There is a reduced risk of therapeutic heat being carried away from the target area by blood flowing through a nearby blood vessel. Another advantage is the elimination of ground pads.

The lesion shape achieved with bipolar radiofrequency ablation can also be beneficial compared to monopolar radiofrequency ablation, such as by being centered at the shaft electrode with the tine ends marking the outer boundary of the lesion, and by having a short axis to long axis ratio closer to one. This makes the lesion shape more predictable and easier to overlap with the tumor shape during treatment. With monopolar radiofrequency ablation using an electrode array, the lesion is formed in the area surrounding the tines of the electrode array, with a greater difference between the short axis and long axis of the lesion.

As used herein, the words proximal and distal express a relationship between two different elements. An element that is designated as being proximal is positioned closer to the external portion of the system, i.e., a portion that does not enter a patient's body. An element that is designated as being distal is positioned closer to the insertion end of the system.

Figure 1B:
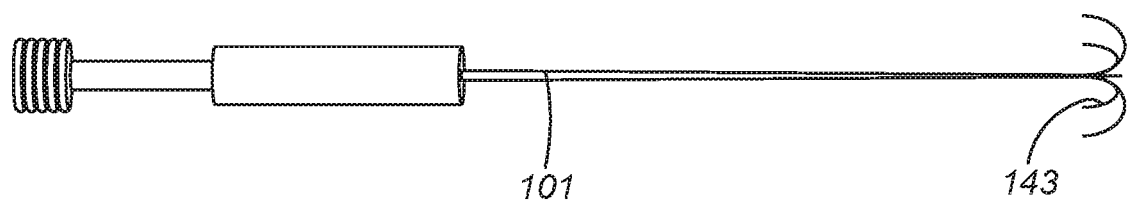
FIG. 1B is a side view of a distal inner electrode assembly, including an electrode array, of a bipolar, open irrigated, radiofrequency ablation system according to some examples.

Turning to the drawings, FIG. 1A is a side view of an outer electrode assembly 100 having a shaft electrode 110 of a radiofrequency ablation probe system according to some examples. FIG. 1B is a side view of an inner electrode assembly 101 of a radiofrequency ablation probe system having an electrode array 143 for a bipolar radiofrequency ablation that is compatible with the system of FIG. 1A. The inner electrode assembly 101 is configured to be received within an inner lumen of the outer electrode assembly 100. The system is configured for attaching to a generator to provide radiofrequency current flow between the electrode array and the shaft electrode. The system is provided with a connection 112 to an irrigation fluid, and defines an open irrigation path which will be further described with reference to other figures.

Figure 1C:
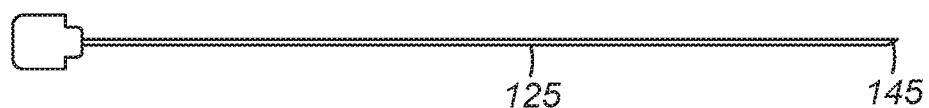
FIG. 1C is a side view of a stylet for use with a radiofrequency ablation system according to some examples.

FIG. 1C is a side view of a stylet 125 that optionally can be provided in a system. In various examples of the technology, the stylet 125 has a sharp trocar tip 145 and can be used with the disclosed radiofrequency ablation system. For example, the stylet 125 can have a radiopaque or echogenic tip, and can be precisely positioned within tissue to be ablated using imaging technology. The stylet can be inserted into a lumen of the inner electrode assembly 101, after which the sharp tip 145 can be used to pierce patient tissue to facilitate entry of the probe assembly 105 into the patient tissue. Alternatively or in addition, the outer electrode assembly 100 or the inner electrode assembly 101 can be provided with a tissue-penetrating sharp tip to facilitate insertion into the body.

Examples of structures for bipolar irrigated radiofrequency ablation featuring differences in the irrigation path or other structures will now be described with respect to the FIGS.

Figure 2A:
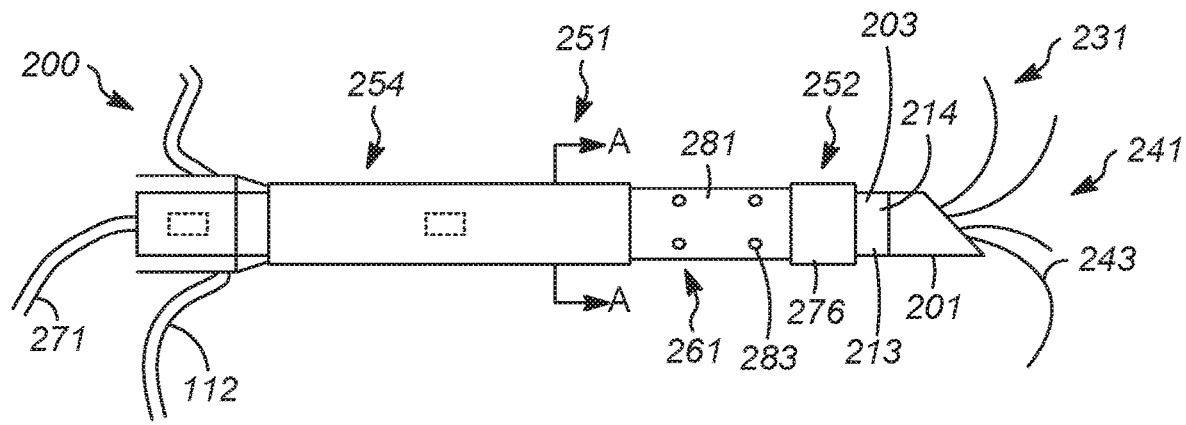
FIG. 2A is a schematic side view of a system for bipolar, open irrigated, radiofrequency ablation according to some examples.
Figure 2B:
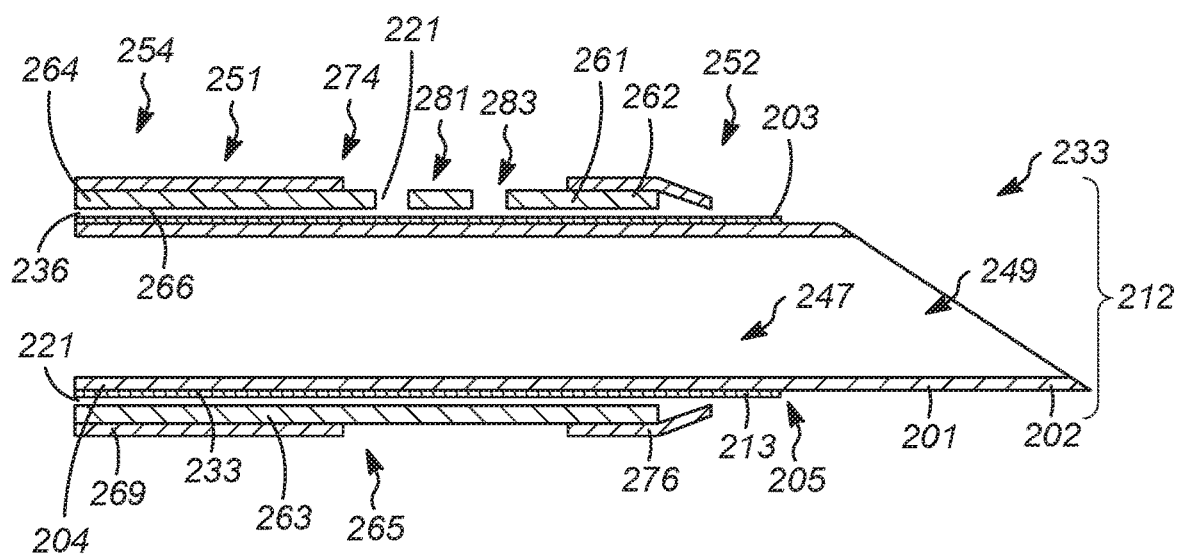
FIG. 2B is a longitudinal cross-sectional view of a portion of the system of FIG. 2A.
Figure 2C:
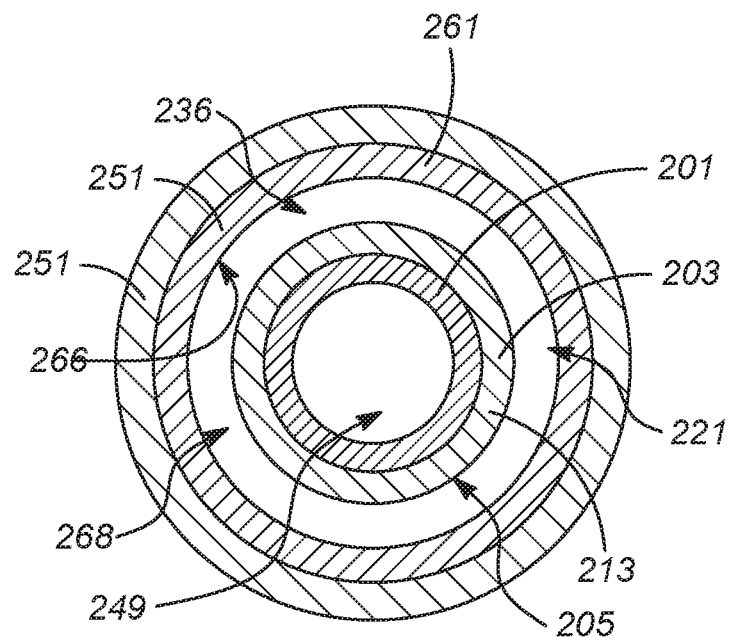
FIG. 2C is a radial cross-sectional view of the system of FIG. 2A along line A-A.

One example of the technology, shown in FIGS. 2A-2C, provides a system 200 for bipolar, open irrigated, radiofrequency ablation. In the example of FIG. 2A, the system includes an elongate inner electrode assembly 212 having an electrode array 241, and an elongate outer electrode assembly 251 having a shaft electrode 281. The electrode array 241 can also be referred to as the distal electrode. The shaft electrode 281 can also be referred to as the proximal electrode or cannula electrode. The inner electrode assembly 212 is configured to be positioned within the lumen 268 of the outer electrode assembly 251, and the system is configured for radiofrequency energy delivery between the electrode array 241 and the shaft electrode 281.

The inner electrode assembly 212 has a distal end 231 and a proximal end 233. The inner electrode assembly 212 includes a sheath 201. The sheath 201 has a proximal end 204 and distal end 202. The sheath 201 has a lumen 247 running through the sheath 201. The lumen 247 ends at lumen opening 249. The lumen 247 holds an electrode array 241 and a first lead 271. The electrode array 241 includes a plurality of electrode tines 243 electrically connected to the first lead 271. In one example, the electrode tines 243 are made of electrically conductive material. The sheath 201 of the inner electrode assembly can be made of stainless steel or other electrically conductive metal with adequate conductivity and strength. One example of a sheath 201, electrode array 241, and first lead 271 that can be used with the systems described herein is the LEVEEN COACCESS™ Needle Electrode, commercially available from Boston Scientific Corporation, Inc. of Marlborough, Massachusetts.

In some examples, the electrode tines 243 are retractable and form a three-dimensional shape, such as the umbrella shape in the example shown in FIG. 1B. Alternatively or in addition, the electrode array 241 includes three or more tines, any number of tines up to and including ten tines, twelve tines, or more tines. Alternatively or in addition, the electrode array 241 is retractable, being movable between a first position contained within the sheath 201 and a second position protruding from the distal end 202 of the sheath 201.

The system further includes an elongate outer electrode assembly 251 having a distal end 252 and a proximal end 254. In some examples, the outer electrode assembly 251 comprises a cannula 261 having a distal end 262 and a proximal end 264. The outer electrode assembly 251 has an inner surface 266 defining a lumen 268. In the example of FIG. 2A-C, the inner surface 266 is the inner surface of the cannula 261. The lumen 268 is configured to receive the inner electrode assembly 212. In some examples, the distal end 202 of the inner electrode assembly 212 protrudes from the lumen 268 at the distal end 252 of the outer electrode assembly 251.

The outer electrode assembly 251 includes a shaft electrode 281 near the distal end 262 of the cannula 261 on an outer surface 265 of the outer electrode assembly 251. In one example, a distal edge of the shaft electrode 281 is spaced away from the distal end of the outer electrode assembly by about 0.5 cm. In some examples, the space is at least about 0.2 cm, at least about 0.3 cm, at most about 1 cm, at most about 0.8 cm, or at most about 0.7 cm. In some examples, the space is at least about 0.2 cm and at most about 0.8 cm, or at least about 0.4 cm and at most about 0.6 cm.

In the example of FIGS. 2A-C, the cannula 261 has a cannula body 263 that can be made of a conducting material, such as a metal including stainless steel. In this example, the shaft electrode 281 is an exposed portion of the outer surface 274 of the cannula body 263. The cannula body 263 can serve as a conductive path from the proximal end 254 of the outer electrode assembly 251 to the shaft electrode 281. The shaft electrode 281 and the electrode array 241 create a first electrode and a second electrode, respectively, in a bipolar radiofrequency ablation system.

In some examples, the cannula body is a stainless steel cannula with an inner diameter of about 0.75 inch and a wall thickness of about 0.0025 inch. Many other dimensions are possible for the cannula.

In some examples, the shaft electrode 281 has a length of about 1.5 cm. In some examples, the electrode length is at least about 0.5 cm, at least about 1 cm, or at least about 1.3 cm. In some examples, the electrode length is at most about 2.5 cm, at most about 1 cm, or at most about 1.7 cm. In some examples, the electrode length is at least about 0.5 cm and at most about 2.5 cm, or at least about 1 cm and at most about 2 cm.

In some examples, the outer surface 265 of the cannula 261 has a proximal insulating segment 269. The proximal insulating segment 269 extends from near the proximal end 264 of the cannula 261 to the shaft electrode 281. The proximal insulating segment 269 can be an insulating tubing layer on an outer surface 274 of the cannula body 263. For example, the insulating tubing layer of the proximal insulating segment 269 can be polyimide tubing, and optionally can be polyimide tubing with braided fibers within a wall of the tubing, polyethylene terephthalate (PET), polyether ether ketone (PEEK), polytetrafluoroethylene (PTFE) (or other fluoropolymers), fluorinated ethylene propylene (FEP), or other electrically insulating materials or combinations of these materials.

In some examples, the outer electrode assembly 251 includes a distal insulating segment 276 at the distal end 262 of the cannula body 263. The distal insulating segment 276 can be an insulating layer on an outer surface 274 of the cannula body 263. The distal insulating segment 276 can be made of polyethylene terephthalate (PET), polyether ether ketone (PEEK), polytetrafluoroethylene (PTFE), fluorinated ethylene propylene (FEP), or combinations of these materials covering the distal end 262 of the cannula body 263.

The distal insulating segment 276 can be made using a heat shrink material. In alternative examples, the distal insulating segment 276 can be a tubing or a coating. Additional examples use an extrusion combined with a heat shrink and reflow techniques. In some examples, the portion of the outer surface 274 of the cannula body 263 that forms the distal insulating segment is rough, textured, or threaded. The rough, textured, or threaded surface can improve adhesion of the insulating materials, such as the heat shrink material. In some examples (not explicitly shown in FIG. 2), the distal insulating segment 276 is configured to create a seal between the insulation sheath 213 and the distal end 262 of the cannula 261 to prevent fluid from exiting the distal end 262 of the cannula 261. In this configuration, irrigation openings 283, described in more detail below, provide the primary irrigation fluid exit path.

The inner electrode assembly 212 has an outer surface 205. In some examples, the inner electrode assembly 212 includes an insulation layer 203 to insulate it from the inner surface of the conductive cannula body 263. In the example of FIGS. 2A-C, the insulation layer 203 is an insulation sheath 213 positioned on the outer surface 205 of the inner electrode assembly 212. The insulation layer 203 can be an insulation sheath 213 positioned on the outer surface 205 of the inner electrode assembly 212. The insulation sheath 213 can be a polyimide insulation sheath, which, in some examples, has an inner diameter of about 0.068 inch and a wall thickness of about 0.0025 inch. Alternatively or in addition, the insulation sheath 213 can include insulators such as polyethylene terephthalate (PET), polyether ether ketone (PEEK), polytetrafluoroethylene (PTFE) (or other fluoropolymers), fluorinated ethylene propylene (FEP), or combinations of these materials.

In some examples, including that of FIG. 2A, a distal segment 214 of the insulation sheath 213 protrudes from a distal end 252 of the outer electrode assembly 251. This configuration isolates the two electrodes of the bipolar radiofrequency ablation system.

The system 200 includes an open irrigation system. A fluid, such as saline, is supplied to an irrigation path at the proximal end of the ablation probe and flows through the system into the body of the patient near the electrodes. The fluid cools both the electrodes and the tissue being ablated. The structure of the irrigation path for the example of FIGS. 2A-2C will now be described.

In the example of FIGS. 2A-C, an irrigation path 221 is defined between the outer surface 205 of the inner electrode assembly 212 and the inner surface 266 of the outer electrode assembly 251. The irrigation path 221 has an annular shape. In some examples, the thickness of the annular irrigation path 221 shown in FIGS. 2A-2C is about 0.01 inch, such as where the outer diameter of the inner electrode assembly 212 is about 0.065 inch and the inner diameter of the cannula 561 is about 0.075 inch.

Furthermore, the irrigation path 221 is defined through irrigation openings 283 in the shaft electrode 281. At the proximal end of the system 200, a fluid enters a gap 236 between the outer surface 205 of the inner electrode assembly 212 and the inner surface 266 of the outer electrode assembly 251. The fluid travels along the outer circumference of the inner electrode assembly 212 toward the distal end 231 of the inner electrode assembly 212. The fluid exits the gap 236 through irrigation openings 283 defined in the shaft electrode 281. The irrigation openings 283 can be irrigation ports that are circular in shape, or a variety of other shapes, and distributed around the outer circumference of the cannula 261.

In a further aspect of the disclosed technology, the system 200 includes an elongate inner electrode assembly 212 having a distal end 231, a proximal end 233, and an outer surface 265. The inner electrode assembly 212 comprises a sheath 201, a first lead 271 within the sheath 201, and an electrode array 241. The electrode array 241 includes three or more electrode tines 243 positioned at the distal end 231 of the inner electrode assembly 212. The electrode tines 243 are electrically connected to the first lead 271, and the electrode array 241 has a first position contained within the sheath 201 and a second position protruding from a distal end 202 of the sheath 201. The system 200 also includes an insulation sleeve 213 positioned on the outer surface 205 of the sheath 201. An elongate outer electrode assembly 251 is provided. The outer electrode assembly 251 has a distal end 252 and a proximal end 254. In some examples, the outer electrode assembly 251 includes a cannula 261 having a cannula body 263 made of an electrically conductive material. The outer electrode assembly 251 has an inner surface 266 defining a lumen 268. A shaft electrode 281 is formed by an exposed segment of the conductive material of the cannula 261 on an outer surface 265 of the outer electrode assembly 251. A proximal insulating segment 269 on the outer surface 274 of the cannula body 263 extends from near the proximal end 264 of the cannula body 263 to the shaft electrode 281. An irrigation path 221 is defined between the outer surface 205 of the inner electrode assembly 212 and the inner surface 266 of the cannula 261. The irrigation path 221 is partially defined through irrigation openings 283 defined in the shaft electrode 281. The inner electrode assembly 212 is configured to be positioned within the lumen 268 of the outer electrode assembly 251, and the system is configured for radiofrequency current flow between the electrode array 241 and the shaft electrode 281.

Figure 3A:
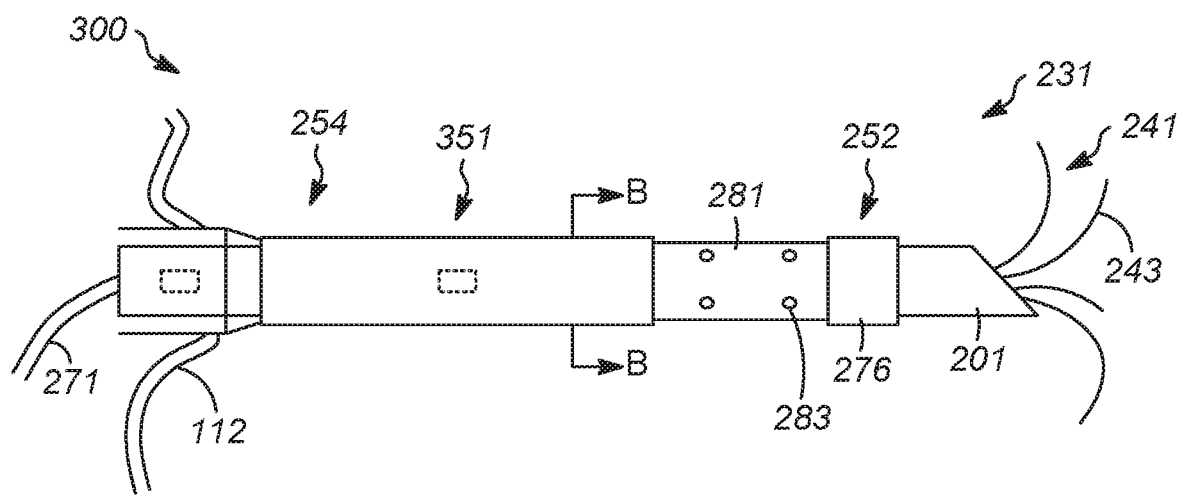
FIG. 3A is a schematic side view of an alternative example of a system for bipolar, open irrigated, radiofrequency ablation according to some examples.
Figure 3B:
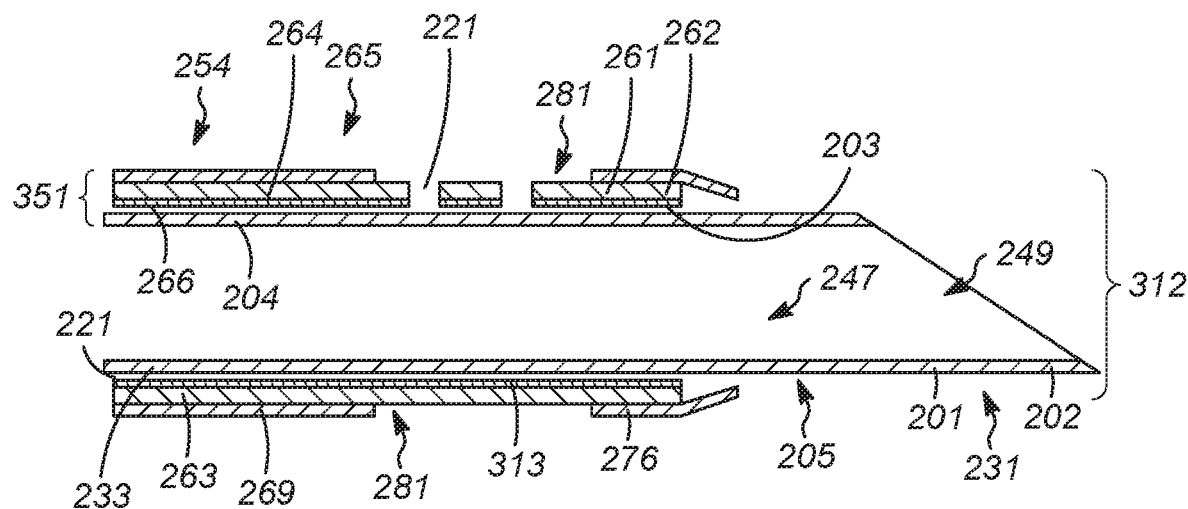
FIG. 3B is a longitudinal cross-sectional view of a portion of the system of FIG. 3A.
Figure 3C:
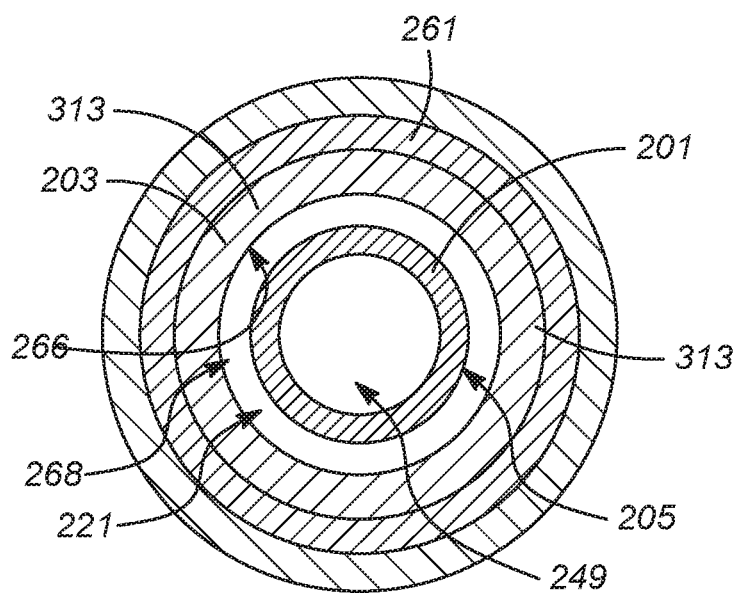
FIG. 3C is a radial cross-sectional view of the system of FIG. 3A along line B-B.

FIGS. 3A-C provide an alternative example of a system for bipolar, irrigated, radiofrequency ablation. Like the example of FIGS. 2A-C, the system 300 includes an inner electrode assembly, an outer electrode assembly, and an irrigation path that allows a fluid to flow through the body of the system and out of the system into patient tissue, where the fluid cools the radiofrequency ablation electrodes and the patient tissue.

In the example of FIGS. 3A-C, the system 300 for bipolar, open irrigated radiofrequency ablation includes an elongate inner electrode assembly 312 having a distal end 231 and a proximal end 233. The inner electrode assembly 312 is configured to be positioned within the lumen 268 of the outer electrode assembly 351, and the system is configured for attaching to a generator to provide radiofrequency current flow between the electrode array 241 and the shaft electrode 281.

The inner electrode assembly 312 has an outer surface 205. The inner electrode assembly 312 includes a sheath 201. The sheath 201, electrode array 241 and other components within the sheath 201 are substantially similar to those described herein with respect to FIGS. 2A-2C, so that description will not be repeated here. A difference between the inner electrode assembly 312 of FIGS. 3A-3C compared to the inner electrode assembly 212 of FIGS. 2A-2C is that the inner electrode assembly 312 does not have an insulation layer forming its outer surface.

The system 300 further includes an elongate outer electrode assembly 351 having a distal end 252 and a proximal end 254. In some examples, the outer electrode assembly 351 includes a cannula 261 having a distal end 262 and a proximal end 264. The outer electrode assembly 351 has an inner surface 266 that defines a lumen 268. The lumen 268 is configured to receive the inner electrode assembly 312.

In some examples, the system 300 includes an insulation layer between the inner electrode assembly 312 and the outer electrode assembly 351. In the example of FIGS. 3A-C, the insulation layer 203 is an insulating coating 313 on the inner surface 266 of the outer electrode assembly 351. Other than the presence of the insulating coating 313, the outer electrode assembly 351 is substantially similar to the outer electrode assembly 251 of FIGS. 2A-2C, such as by having a conductive cannula body 263, and an exposed portion of the cannula body 263 forming the shaft electrode 281. As a result, the description of the components and structure of the outer electrode assembly 351 that are shared in common with the outer electrode assembly 251 will not be repeated here.

The system 300 includes an open irrigation system. A fluid, such as saline, is inserted into the proximal end of the ablation probe and flows through the system into the body of the patient. The fluid cools both the electrodes and the tissue being ablated. In the example of FIGS. 3A-C, the irrigation path 221 is defined between the outer surface 205 of the inner electrode assembly 312 and the inner surface 266 of the outer electrode assembly 351. Furthermore, like in the examples of FIGS. 2A-2C, the irrigation path 221 is defined through irrigation openings 283 in the shaft electrode 281. The irrigation path 221 of FIGS. 3A-3C is similar to the irrigation path 221 of FIGS. 2A-2C, so that full description will not be repeated here.

Figure 4A:
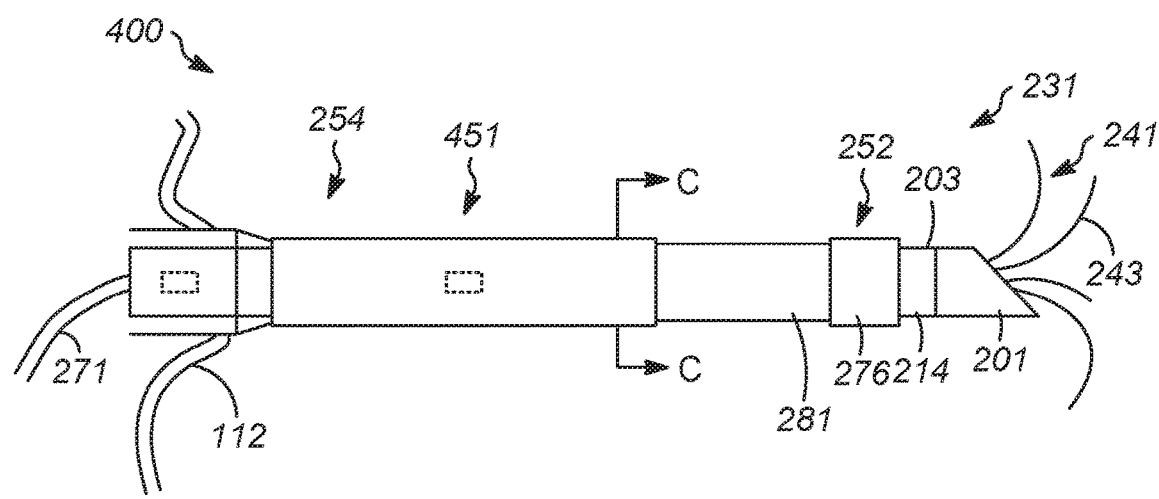
FIG. 4A is a schematic side view of an alternative example of a system for bipolar, open irrigated, radiofrequency ablation according to some examples.
Figure 4B:
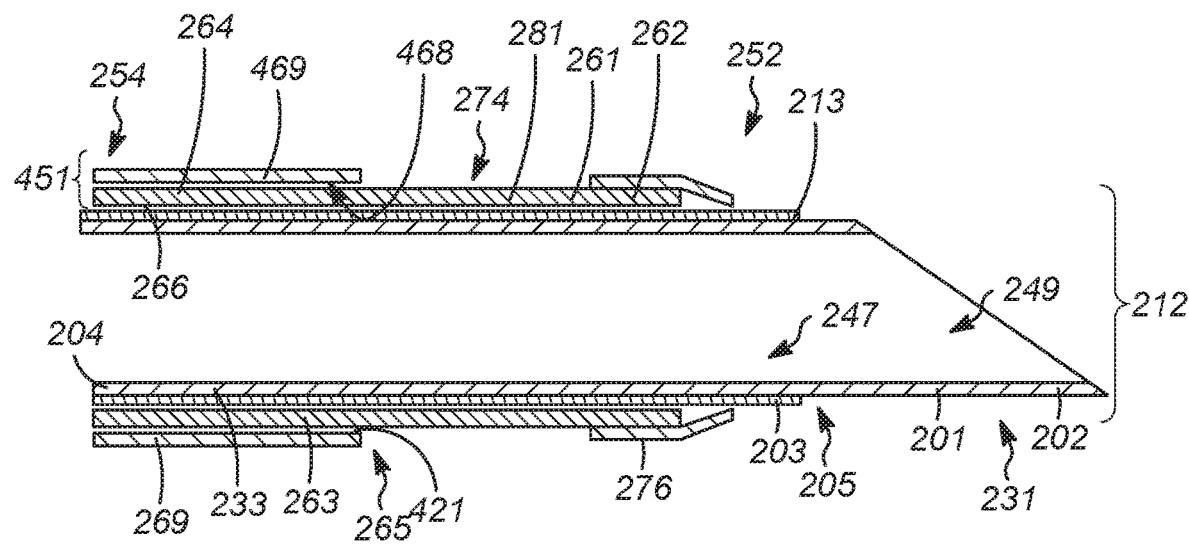
FIG. 4B is a longitudinal cross-sectional view of a portion of the system of FIG. 4A.
Figure 4C:
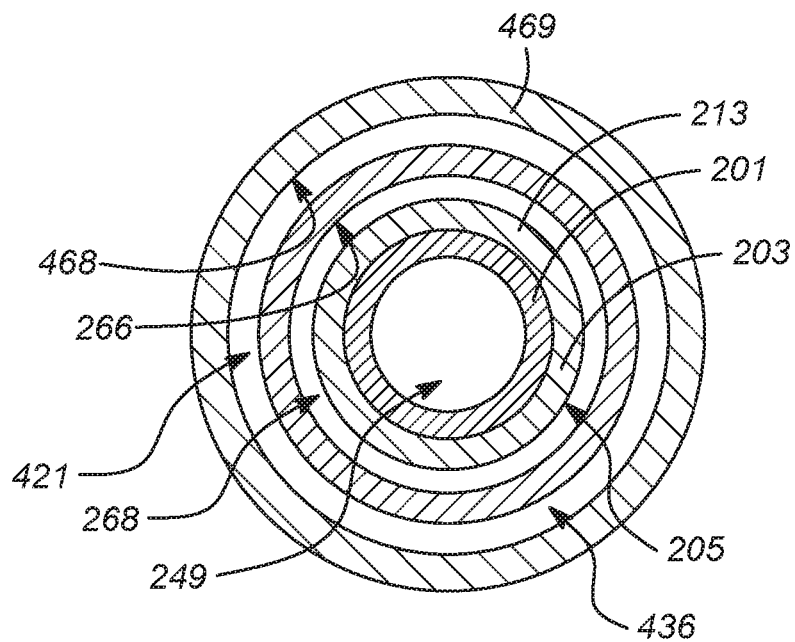
FIG. 4C is a radial cross-sectional view of the system of FIG. 4A along line C-C.

FIGS. 4A-C provide an alternative example of a system 400 for bipolar, irrigated, radiofrequency ablation. Like the examples of FIGS. 2A-C and FIGS. 3A-C, the system 400 includes an inner electrode assembly 212, an outer electrode assembly 451, and an irrigation path that allows a fluid to flow through the body of the system and out of the system into patient tissue, where the fluid cools the radiofrequency ablation electrodes and the patient tissue. Also like the examples of FIGS. 2A-C and FIGS. 3A-C, the outer electrode assembly 451 includes a cannula 261 having a cannula body 263 made of a conductive material and a shaft electrode 281 is an exposed portion of the cannula body. The cannula 261 can be substantially similar to the cannula 261 of FIGS. 2A-2C and 3A-3C, so that description will not be repeated here.

The example of FIGS. 4A-C provides a system 400 for bipolar, irrigated, radiofrequency ablation. The inner electrode assembly 212 as shown in FIGS. 4A-C can be substantially the same as described with respect to FIGS. 2A-C, and thus the details will not be repeated here.

The system 400 further includes an elongate outer electrode assembly 451 having a distal end 252 and a proximal end 254. The outer electrode assembly 451 includes a cannula 261 having a distal end 262 and a proximal end 264. The outer electrode assembly 451 has an inner surface 266 defining a lumen 268. In the example of FIGS. 4A-C, the inner surface 266 is the inner surface of the cannula 261. The lumen 268 is configured to receive the inner electrode assembly 212. In some examples, the distal end 202 of the inner electrode assembly 212 protrudes from the lumen 268 at the distal end 252 of the outer electrode assembly 451.

The outer electrode assembly 451 includes a shaft electrode 281 near the distal end 262 of the cannula 261 on an outer surface 265 of the outer electrode assembly 451.

The system 400 includes an open irrigation system. A fluid, such as saline, is inserted into the proximal end of the ablation probe and flows through the system into the body of the patient. The fluid cools both the electrodes and the tissue being ablated. An irrigation path 421 is defined between the outer surface 205 of the inner electrode assembly 212 and an outer surface 265 of the outer electrode assembly 451.

In the example of FIGS. 4A-C, the outer electrode assembly 451 includes a proximal insulating segment 469 adjacent to an outer surface 274 of the cannula. A gap 436 exists between the cannula 261 and the insulating segment 469. The proximal insulating segment 469 extends from near the proximal end 264 of the cannula 261 to the shaft electrode 281. The irrigation path 421 is defined in the gap 436 between the outer surface 274 of the cannula and the inner surface 468 of the proximal insulating segment 469.

The proximal insulating segment 469 can be an insulating tubing positioned around the circumference of the cannula body 263. For example, the insulating tubing of the proximal insulating segment 469 can be polyimide tubing, and optionally can be polyimide tubing with braided fibers within a wall of the tubing.

In some examples, the outer electrode assembly 451 includes a distal insulating segment 276 at the distal end 262 of the cannula body 263, which is substantially similar to the distal insulating segment described with respect to FIGS. 2A-2C and FIGS. 3A-3C.

Figure 5A:
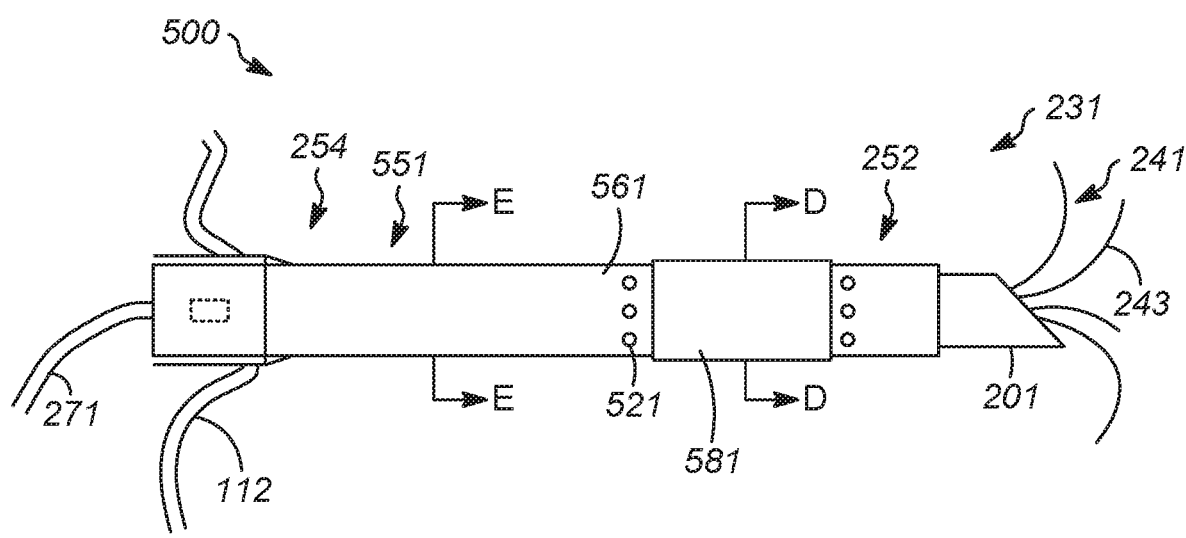
FIG. 5A is a schematic side view of an alternative example of a system for bipolar, open irrigated, radiofrequency ablation according to some examples.
Figure 5B:
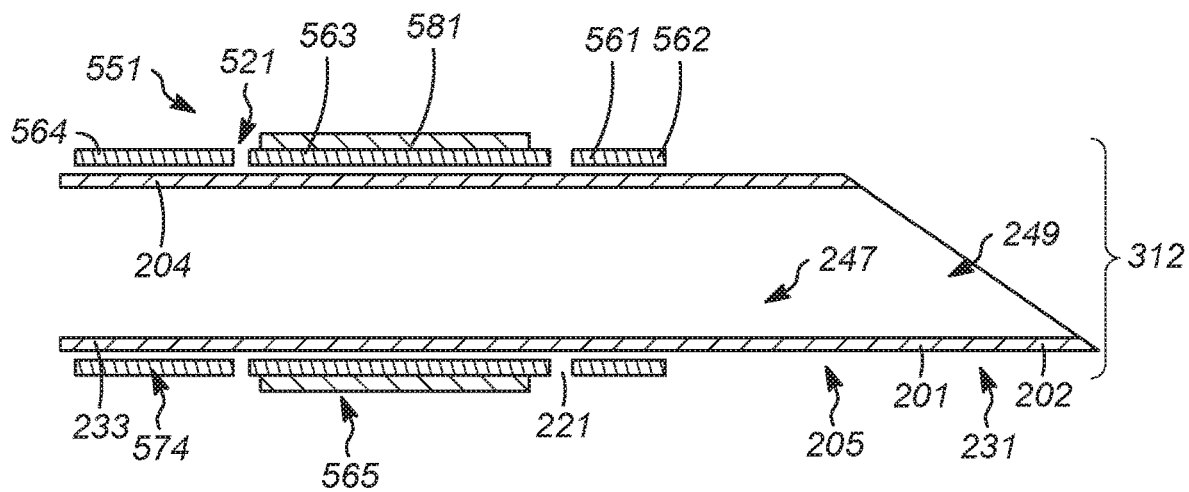
FIG. 5B is a longitudinal cross-sectional view of a portion of the system of FIG. 5A.
Figure 5C:
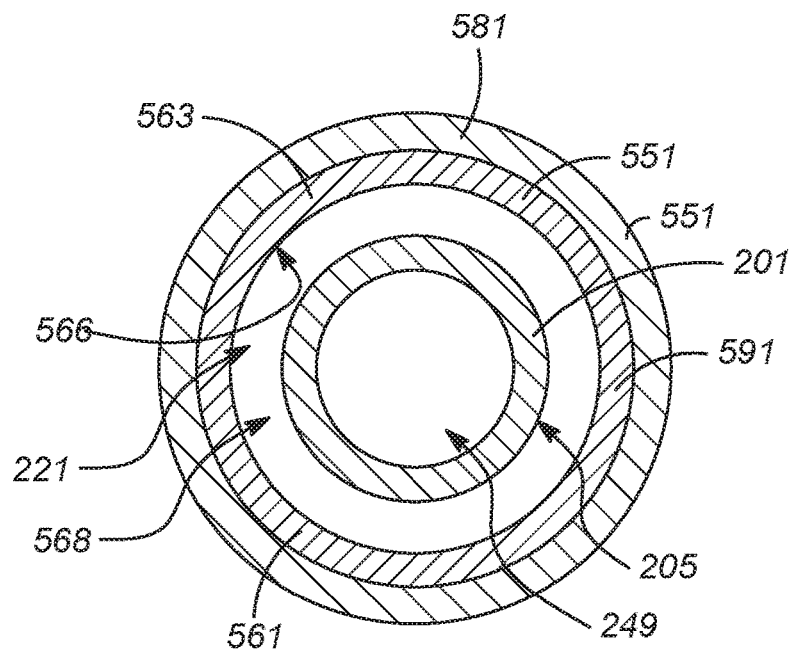
FIG. 5C is a radial cross-sectional view of the system of FIG. 5A along line D-D.

FIGS. 5A-C provide an alternative example of a system for bipolar, irrigated radiofrequency ablation. Like the example of FIGS. 2A-C, 3A-C, and 4A-C, the system 500 includes an inner electrode assembly, an outer electrode assembly, and an irrigation path that allows a fluid to flow through the body of the system and out of the system into patient tissue, where the fluid cools the radiofrequency ablation electrodes and the patient tissue.

In the example of FIGS. 5A-C, the system 500 for bipolar, irrigated radiofrequency ablation includes an elongate inner electrode assembly 312 having a distal end 231 and a proximal end 233. The inner electrode assembly 312 as shown in FIGS. 5A-C can be substantially the same as described with respect to FIGS. 3A-C, and thus the details will not be repeated here. The system 500 further includes an elongate outer electrode assembly 551 having a distal end 252 and a proximal end 254. The outer electrode assembly 551 includes a cannula 561 having a distal end 562 and a proximal end 564. The outer electrode assembly 551 has an inner surface 566 defining a lumen 568. In the example of FIGS. 5A-C, the inner surface 266 is the inner surface of the cannula 561.

The system 500 includes an open irrigation system. A fluid, such as saline, is inserted into the proximal end of the ablation probe and flows through the system into the body of the patient. The fluid cools both the electrodes and the tissue being ablated. An irrigation path 221 is defined between the outer surface 205 of the inner electrode assembly 312 and an outer surface 565 of the outer electrode assembly 551. In some examples, the irrigation path 221 is defined between the outer surface of the sheath 201 and the inner surface 566 of the outer electrode assembly 551.

In the examples of FIGS. 5A-E, the cannula 561 has a cannula body 563 made of an insulating material. For example, the cannula body 563 can be polyimide tubing, and optionally can be polyimide tubing with braided fibers within a wall of the tubing. Alternatively or in addition, the cannula body 563 can comprise insulators such as polyether ether ketone (PEEK), polytetrafluoroethylene (PTFE) (or other fluoropolymers), or combinations of these materials. The outer electrode assembly 551 has a shaft electrode 581 near the distal end 562 of the cannula 561 on an outer surface 565 of the outer electrode assembly 551.

In the examples of FIGS. 5A-E, the shaft electrode 581 is an electrically conductive structure attached to an outer surface 574 of the cannula body 563. Options for the material of the shaft electrode 581 include metal, platinum, stainless steel, or the like. The shaft electrode 581 can have a ring shape. In addition or alternatively, the electrode is a stainless steel or platinum ring with a wall thickness of about 0.001 inch and a length of about 1.5 cm.

Figure 5D:
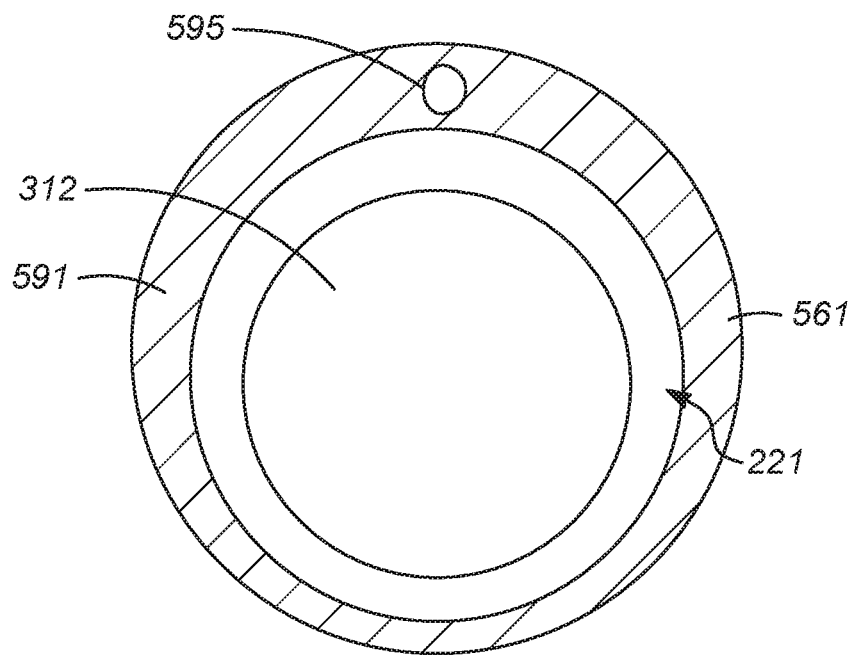
FIG. 5D is a radial cross-sectional view of the system of FIG. 5A along line E-E according to some examples.
Figure 5E:
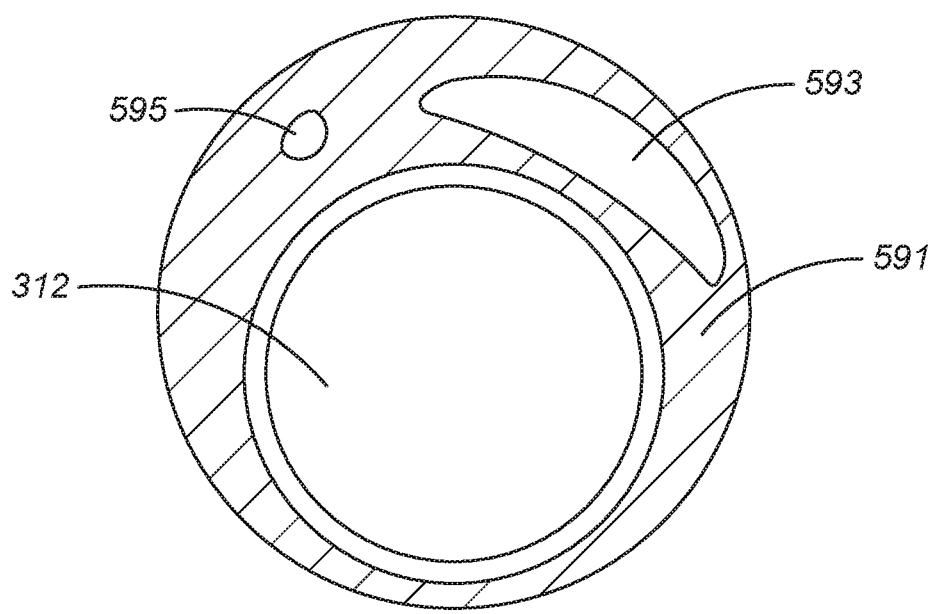
FIG. 5E is a cross-sectional view of a system for bipolar, open irrigated, radiofrequency ablation according to some examples.

The system 500 includes a conductive path from the proximal end 254 of the outer electrode assembly 551 to the shaft electrode 581. In some examples, as shown in FIGS. 5D-E, a second lead 595 provides a conductive path from the proximal end 564 of the cannula 561 to the shaft electrode 581 within a wall 591 of the cannula body 563.

The cannula 561 defines irrigation openings 521 near the shaft electrode 581. An irrigation path 221 is defined between the inner surface 566 of the cannula 561 and the outer surface 205 of the inner electrode assembly 312. In some examples, thickness of the annular irrigation path 221 shown in FIGS. 5A-D is about 0.01 inch, such as where the outer diameter of the inner electrode assembly 312 is about 0.065 inch and the inner diameter of the cannula 561 is about 0.075 inch.

The irrigation path 221 is further defined through the irrigation openings 521. In some examples, irrigation openings 521 are located along the length of the cannula 561 on a proximal side of the shaft electrode 581. Alternatively or in addition, irrigation openings 521 can be located along the length of the cannula 561 on a distal side of the shaft electrode 581. In various example, a distance between the irrigation openings 521 and a nearest edge of the shaft electrode 581 is between about 0.1 cm and 0.5 cm, inclusive. In some examples, the distance is at most about 0.5 cm or at most about 0.3 cm. In some examples, the distance is at least about 0.1 cm.

Alternatively or in addition, irrigation openings are defined through the shaft electrode 581 and through the cannula body 563 underlying the shaft electrode 581. This is not shown in the drawings.

In addition or alternatively, an irrigation path can be defined within a wall 591 of the cannula 561 to supply irrigation fluid to the irrigation openings 521 of FIG. 5A. FIG. 5E shows a radial cross section along line E-E in FIG. 5A, where an irrigation channel 593 is illustrated in the wall 591, as an alternative to the irrigation path 221 structure shown in FIG. 5D. The irrigation path 593 is defined within a wall 591 of the cannula 561 and through the irrigation openings 521. In this case, the irrigation path 593 is in fluid communication with one or more irrigation openings 521 shown in FIG. 5A. FIGS. 5A-C are consistent with the example of FIG. 5E.

Irrigation Openings

Irrigation openings are provided in different configurations in the FIGS., including irrigation openings 283 of FIGS. 2A-C and FIGS. 3A-C, and irrigation openings 521 of FIGS. 5A-E. In various examples, the irrigation openings are located along the length of the outer electrode assembly. Some examples provide irrigation openings along the length of the shaft electrode. Alternative examples provide irrigation openings proximal and/or distal to the shaft electrode. The irrigation openings provide a path for coolant to exit. In various examples, the irrigation openings are circular. In alternative examples, the irrigation openings can be oval or a variety of other shapes. The irrigation openings can have a diameter of about 0.015 inch, at least about 0.005 inch, at least about 0.010 inch, at least about 0.012 inch, at most about 0.025 inch, at most about 0.020 inch, at least about 0.005 inch and at most about 0.025 inch, or at least about 0.010 inch and at most about 0.020 inch.

The irrigation openings 283 of FIGS. 2A-C and FIGS. 3A-C are defined through the shaft electrode 281. In the example arrangements of FIGS. 2A-C and FIGS. 3A-C, the irrigation openings 283 are arranged in two rows extending radially around the electrode with three holes in each row. Within each row, the irrigation openings are 120 degrees apart. In various examples, one, two, three or four rows of irrigation openings could extend radially around the shaft electrode, and one, two, three, four or five irrigation openings could be present in each row.

The two rows of irrigation openings 283 of FIGS. 2A-C and FIGS. 3A-C are 2 mm and 7 mm from the distal edge of the shaft electrode. Other spacing is possible in different examples.

The outer electrode assembly 100 of FIGS. 2A-C and FIGS. 3A-C includes the distal insulating portion 276 at the distal end of the outer electrode assembly, which plays a role in directing flow of the irrigation fluid out through the irrigation openings 283. The distal insulating portion 276 extends off of the distal end of the outer electrode assembly and tapers toward its distal end to seal against the inner electrode assembly and prevent irrigation fluid from flowing out of the distal end of the outer electrode assembly.

Radiofrequency Ablation Method

Figure 6:
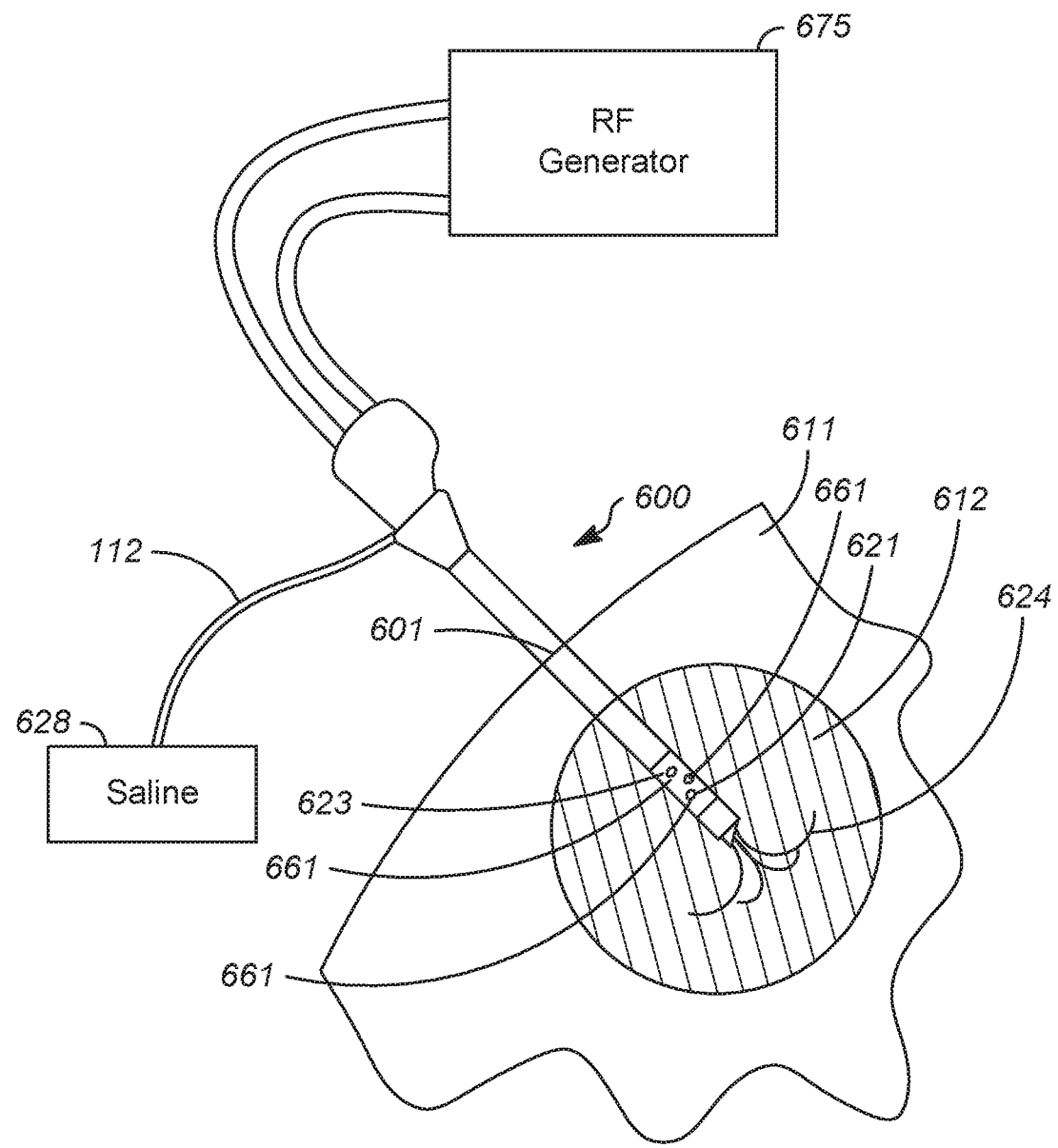
FIG. 6 is a schematic view of a system for performing radiofrequency ablation according to some examples.

The various examples of radiofrequency ablation system as described herein can be used to perform a method of radiofrequency ablation. FIG. 6 is a schematic view of a system for performing radiofrequency ablation according to some examples. The method includes providing an elongate inner electrode assembly having a distal end, a proximal end, and an outer surface. The inner electrode assembly can be that of any of the examples of FIGS. 2A-5E. The inner electrode assembly includes a sheath and an electrode array comprising three or more electrode tines positioned at the distal end of the inner electrode assembly and connected to the first lead. The electrode array is movable between a first position contained within the sheath and a second position protruding from a distal end of the sheath.

The method further includes providing an outer electrode assembly having a distal end and a proximal end and comprising a cannula having a distal end and a proximal end. The cannula has an inner surface defining a lumen. A shaft electrode is provided near the distal end of the cannula on an outer surface of the outer electrode assembly. A conductive path runs from the proximal end of the outer electrode assembly to the shaft electrode.

The method includes positioning the inner electrode assembly within the cannula of the outer electrode assembly, attaching an irrigation source to an irrigation path defined between the outer surface of the inner electrode assembly and the outer surface of the outer electrode assembly. The method further includes providing fluid flow through the irrigation path and attaching the system to a generator and providing radiofrequency current flow between the electrode array and the shaft electrode.

As shown in FIG. 6, a radiofrequency ablation system 600 includes a probe 601. The probe 601 is inserted into patient tissue 611 and into a volume of tissue 612 that is desired to be ablated. The system 600 includes tine electrodes 624 that protrude from a distal end of the probe 601. A second electrode 623 along the body of the probe 601, along with the electrodes 624, are configured to provide bipolar radiofrequency ablation. A source of radiofrequency energy 675 is provided. The radiofrequency energy source 675 can be, for example an RF 3000™ Generator, manufactured by Boston Scientific, Inc. of Marlborough, Massachusetts.

An irrigation source, such as a saline source 628, is used to inject saline through the probe 601 into the patient tissue 612. In some examples, the saline is a 0.9% saline solution. Other concentrations of saline solution can be used. An irrigation path 621 allows a fluid to irrigate the tissue to be ablated 612, as indicated by arrows 661. When radiofrequency energy is transferred into patient tissue, the tissue 612 becomes heated. The irrigation fluid regulates the temperature, reducing overheating, and allowing a larger area to be ablated in a shorter period of time.

In some examples, the flow rate of the fluid through the irrigation path 621 can be about 0.5 mL per minute. In some examples, the flow rate of the fluid through the irrigation path 621 can be about at least about 0.3 mL per minute and at most about 2 mL per minute, at least about 0.5 mL per minute and at most about 2 mL per minute, or at least about 1.0 mL per minute and at most about 2 mL per minute.

One example method of irrigated, bipolar radiofrequency ablation will now be described, where the system 600 is positioned within the patient tissue 612 to be ablated and the electrodes are electrically connected to the radiofrequency generator 675. Before beginning ablation, saline irrigation is started at a rate of about 0.5 ml/min for about one minute. Different amounts of saline and different rates of saline irrigation could be used before starting radiofrequency ablation, such as irrigating with 2 mL of saline. After the initial saline infusion, radiofrequency ablation is started at 15 Watts while saline irrigation continues. The power of the radiofrequency ablation is increased by 5 Watts every 30 seconds, as long as the tissue impedance decreases over the previous 30 seconds. An example of a minimum decrease required by this protocol is 3 Ohms. When the impedance decrease plateaus, which is likely to occur at about 25-30 Watts, then the power is increased by 2 Watts every 30 seconds. When impedance starts to increase, the power is no longer adjusted. The generator is allowed to adjust itself down in response to the increasing impedance according to its programming. After 10 minutes, the radiofrequency ablation generator is stopped, although it may have shut itself down by that time according to its programming. For a larger lesion, the clinician can wait for 30 seconds and then restart this protocol at 50% of highest power used so far.

In the second round of the protocol for larger lesions, the power of the radiofrequency ablation is increased by 5 Watts every 30 seconds, as long as the tissue impedance decreases over the previous 30 seconds. When the impedance decrease plateaus, such as by decreasing by about 25-30 Watts every 30 seconds, then the power is increased by 2 Watts every 30 seconds. When impedance starts to increase, the power is no longer adjusted. The generator is allowed to adjust itself down in response to the increasing impedance according to its programming. After 10 minutes, the radiofrequency ablation generator is stopped, although it may have shut itself down by that time according to its programming.

The present disclosure enables the creation of a larger lesion, such as a minimum of 3 cm on one axis, and often 5 cm by 5 cm, in a short application period such as about 10 minutes, using a single probe with lower power on the order of about 40 Watts or less, with no grounding pads, no risk of skin burns, and less heat transferred to the non-target portions of the body.

Some of the FIGS. are schematic in nature and are not drawn to scale. Certain features are shown larger than their scale and certain features are omitted from some views for ease of illustration.

It should be noted that, as used in this specification and the appended claims, the singular forms include the plural unless the context clearly dictates otherwise. It should also be noted that the term "or" is generally employed in its sense including "and/or" unless the content clearly dictates otherwise.

All publications and patent applications referenced in this specification are herein incorporated by reference in their entirety.

The invention has been described with reference to various specific and preferred embodiments and techniques. However, it should be understood that many variations and modifications may be made while remaining within the spirit and scope of the invention.

What is claimed is:

1. A system for bipolar, irrigated, radiofrequency ablation comprising:
   an elongate inner electrode assembly having a distal end, a proximal end, and an outer surface, the inner electrode assembly comprising:
      a sheath,
      a first lead within the sheath, and
      an electrode array comprising three or more electrode tines positioned at the distal end of the inner electrode assembly and electrically connected to the first lead, wherein the electrode array is moveable between a first position contained within the sheath and a second position protruding from a distal end of the sheath;
   an elongate outer electrode assembly having a distal end and a proximal end and comprising
   a cannula having a distal end and a proximal end, the outer electrode assembly comprising:
      an inner surface defining a lumen,
      a shaft electrode near the distal end of the cannula on an outer surface of the outer electrode assembly,
      a distal insulating segment at the distal end of the cannula, and
      a conductive path from the proximal end of the outer electrode assembly to the shaft electrode; and
   an irrigation path defined between the outer surface of the inner electrode assembly and an outer surface of the outer electrode assembly;
   wherein the inner electrode assembly is configured to be positioned within the lumen of the outer electrode assembly, and wherein the system is configured for attaching to a generator to provide radiofrequency current flow between the electrode array and the shaft electrode.

2. The system of claim 1 further comprising an insulation layer between the inner electrode assembly and the outer electrode assembly, wherein the insulation layer is selected from a group consisting of:
   an insulation sheath positioned on the outer surface of the inner electrode assembly, and
   an insulating coating on the inner surface of the outer electrode assembly.

3. The system of claim 1 further comprising an insulation layer between the inner electrode assembly and the outer electrode assembly, wherein the insulation layer comprises an insulation sheath positioned on the outer surface of the inner electrode assembly, wherein a distal segment of the insulation layer protrudes from the distal end of the outer electrode assembly.

4. The system of claim 1 wherein the irrigation path is defined between an outer surface of the inner electrode assembly and the inner surface of the outer electrode assembly, wherein the irrigation path is further defined by irrigation openings defined in the shaft electrode.

5. The system of claim 1 wherein the outer electrode assembly comprises a proximal insulating segment adjacent to an outer surface of the cannula, the proximal insulating segment extending from near the proximal end of the cannula to the shaft electrode, wherein the irrigation path is defined between the outer surface of the cannula and an inner surface of the proximal insulating segment.

6. The system of claim 1 wherein the shaft electrode is attached to the outer surface of the cannula, wherein the cannula defines irrigation openings near the shaft electrode, wherein the irrigation path is defined between the inner surface of the cannula and the outer surface of the inner electrode assembly.

7. The system of claim 1 wherein the shaft electrode is attached to the outer surface of the cannula, wherein the cannula defines irrigation openings near the shaft electrode, wherein the irrigation path is defined within a wall of the cannula and through the irrigation openings.

8. The system of claim 1, wherein the irrigation path is defined through irrigation openings defined in the shaft electrode or defined near the shaft electrode.

9. The system of claim 1 wherein the cannula comprises:
   a cannula body made of a conductive material, wherein the shaft electrode is formed by an exposed segment of the conductive material, and
   a proximal insulating segment on an outer surface of the cannula body extending from near the proximal end of the cannula body to the shaft electrode, the proximal insulating segment comprising an insulating tubing layer on an outer surface of the cannula body.

10. The system of claim 9 wherein the cannula body comprises stainless steel and wherein at least a portion of the outer surface of the cannula body is rough, textured, or threaded.

11. The system of claim 9 wherein the insulating tubing layer of the proximal insulating segment is selected from the group consisting of:
   polyimide tubing;
   polyimide tubing with braided fibers within a wall of the tubing;
   polyethylene terephthalate (PET);
   polyether ether ketone (PEEK); and
   polytetrafluoroethylene (PTFE).

12. The system of claim 1 wherein the distal insulating segment is selected from the group consisting of a heat shrink material, polyether ether ketone (PEEK), polytetrafluoroethylene (PTFE), fluoropolymers, fluorinated ethylene propylene (FEP), polyethylene terephthalate (PET), and combinations of these materials.

13. The system of claim 1 wherein the cannula comprises:
   a cannula body made of an insulating material, wherein the shaft electrode is attached to an outer surface of the cannula body; and
   a second lead providing a conductive path from the proximal end of the cannula to the shaft electrode within a wall of the cannula body.

14. The system of claim 1 wherein the inner electrode assembly defines a central passage and an opening at the distal end of the inner electrode assembly, the system further comprising a stylet configured to be received within the central passage of the inner electrode assembly, the stylet comprising a sharp tip.

15. The system of claim 1, wherein the irrigation path defines an exit path for open irrigation.

16. A system for bipolar, irrigated, radiofrequency ablation comprising:
- an elongate inner electrode assembly having a distal end, a proximal end, and an outer surface, the inner electrode assembly comprising:
  - a sheath,
  - a first lead within the sheath,
  - an electrode array disposed within a lumen of the sheath, the electrode array comprising three or more electrode tines positioned at the distal end of the inner electrode assembly and electrically connected to the first lead, wherein the electrode array has a first position contained within the sheath and a second position protruding from a distal end of the sheath, and
  - an insulation sleeve positioned on the outer surface of the sheath;
- an elongate outer electrode assembly having a distal end and a proximal end and comprising:
  - a cannula having a cannula body made of an electrically conductive material, wherein a distal end of the cannula body is rough or textured,
  - an inner surface defining a lumen,
  - a shaft electrode formed by an exposed segment of the conductive material of the cannula on an outer surface of the outer electrode assembly,
  - a distal insulating segment on the outer surface of the cannula body extending from the distal end of the cannula body to the shaft electrode, wherein the distal insulating segment overlaps the rough or textured distal end of the cannula body, and
  - a proximal insulating segment on the outer surface of the cannula body extending from near the proximal end of the cannula body to the shaft electrode; and
- an irrigation path defined between the outer surface of the inner electrode assembly and the inner surface of the cannula, the irrigation path further defined through irrigation openings defined in the shaft electrode;
- wherein the inner electrode assembly is configured to be positioned within the lumen of the outer electrode assembly, wherein the system is configured for attaching to a generator to provide radiofrequency current flow between the electrode array and the shaft electrode.

17. The system of claim 16, wherein the irrigation path is further defined by irrigation openings defined in the shaft electrode.

18. The system of claim 16, further comprising an insulation layer between the inner electrode assembly and the outer electrode assembly.

19. A radiofrequency ablation method comprising:
- providing an elongate inner electrode assembly having a distal end, a proximal end, and an outer surface, the inner electrode assembly comprising
  - a sheath,
  - an electrode array disposed within a lumen of the sheath, the electrode array comprising three or more electrode tines positioned at the distal end of the inner electrode assembly and electrically connected to a first lead, wherein the electrode array is moveable between a first position contained within the sheath and a second position protruding from a distal end of the sheath, and
  - an insulation sleeve positioned on the outer surface of the sheath;
- providing an elongate outer electrode assembly having a distal end and a proximal end and comprising a cannula having a distal end and a proximal end, the cannula comprising:
  - an inner surface defining a lumen,
  - a shaft electrode near the distal end of the cannula on an outer surface of the outer electrode assembly,
  - a conductive path from the proximal end of the cannula to the shaft electrode; and
  - a distal insulating segment on the outer surface of the cannula extending from the distal end of the cannula to the shaft electrode, wherein the distal insulating segment is configured to form a seal between the insulation sleeve and the distal end of the cannula;
- positioning the inner electrode assembly within the cannula of the outer electrode assembly;
- attaching an irrigation source to an irrigation path defined between the outer surface of the inner electrode assembly and the outer surface of the outer electrode assembly;
- providing fluid flow through the irrigation path; and
- attaching the inner electrode assembly and outer electrode assembly to a generator and providing radiofrequency current flow between the electrode array and the shaft electrode.

* * * * *